(12) United States Patent
Wu et al.

(10) Patent No.: US 12,249,414 B2
(45) Date of Patent: *Mar. 11, 2025

(54) MENTAL HEALTH PREDICTIVE MODEL MANAGEMENT SYSTEM

(71) Applicant: Evernorth Strategic Development, Inc., St. Louis, MO (US)

(72) Inventors: Gang Wu, Ballwin, MO (US); Christopher G. Lehmuth, St. Louis, MO (US); Amit K. Bothra, Wildwood, MO (US); Pritesh J. Shah, Paramus, NJ (US); Zachary A. Goodman, St. Louis, MO (US); Kelcey A. Blair, Chattanooga, TN (US); Callie S. Carter, St. Louis, MO (US); Jackie L. Ahlstrom, Inver Grove Heights, MN (US); Amy C. Gross, Bloomington, MN (US); Jeremy A. Rower, West Linn, OR (US); Rochelle R. Henderson, Edwardsville, IL (US); Snezana Mahon, Creve Coeur, MO (US)

(73) Assignee: Evernorth Strategic Development, Inc., St. Louis, MO (US)

(*) Notice: Subject to any disclaimer, the term of this patent is extended or adjusted under 35 U.S.C. 154(b) by 635 days.

This patent is subject to a terminal disclaimer.

(21) Appl. No.: 17/528,732

(22) Filed: Nov. 17, 2021

(65) Prior Publication Data

US 2022/0157435 A1 May 19, 2022

Related U.S. Application Data

(63) Continuation-in-part of application No. 17/386,223, filed on Jul. 27, 2021, now Pat. No. 12,009,087.

(Continued)

(51) Int. Cl.
*G16H 20/10* (2018.01)
*G16H 10/60* (2018.01)
(Continued)

(52) U.S. Cl.
CPC ............ *G16H 20/70* (2018.01); *G16H 10/60* (2018.01); *G16H 20/10* (2018.01); *G16H 50/20* (2018.01);
(Continued)

(58) Field of Classification Search
CPC ........ G06Q 30/02; G06Q 40/08; G06N 20/00; G16H 10/60; G16H 20/10; G16H 50/20;
(Continued)

(56) References Cited

U.S. PATENT DOCUMENTS 8,391,989 B2 3/2013 Hatlestad
8,799,030 B1 8/2014 Chen
(Continued)

FOREIGN PATENT DOCUMENTS

EP 3145407 A2 * 3/2017 ............. A61B 5/103
EP 36000361 A 2/2020
(Continued)

OTHER PUBLICATIONS

Medical diagnostic and treatment module for advanced patient management (English) (United States)), The IP.com Prior Art Database, Feb. 27, 2008 (Year: 2008).*

(Continued)

*Primary Examiner* — Marilyn G Macasiano
(74) *Attorney, Agent, or Firm* — Jordan IP Law PC

(57) ABSTRACT

Systems and methods herein describe a mental health management system. The mental health management system accesses patient data associated with a patient from a database, determines that the patient is associated with a trigger event, identifies a category associated with the trigger (Continued)

event, generates a notification based on the trigger event and the identified category, validates the notification based on a notification history and transmits the notification to a computing device.

20 Claims, 15 Drawing Sheets

Related U.S. Application Data

(60) Provisional application No. 63/115,464, filed on Nov. 18, 2020.

(51) Int. Cl.
| | |
|---|---|
| *G16H 20/70* | (2018.01) |
| *G16H 50/20* | (2018.01) |
| *A61B 5/16* | (2006.01) |
| *G06Q 40/08* | (2012.01) |
| *G16H 40/20* | (2018.01) |

(52) U.S. Cl.
CPC .............. *A61B 5/165* (2013.01); *G06Q 40/08* (2013.01); *G16H 40/20* (2018.01)

(58) Field of Classification Search
CPC ........ G16H 50/30; G16H 70/40; G16H 20/00; G16H 20/70; G16H 40/20; G16H 40/67; G16H 15/00
See application file for complete search history.

(56) References Cited

U.S. PATENT DOCUMENTS

| | | | | |
|---|---|---|---|---|
| 9,536,052 | B2* | 1/2017 | Amarasingham | G16H 50/30 |
| 10,426,380 | B2 | 10/2019 | Schindhelm | |
| 10,445,886 | B2 | 10/2019 | Hsieh | |
| 10,649,983 | B1 | 5/2020 | Lequeux | |
| 10,734,105 | B1* | 8/2020 | Neumann | G06F 18/23213 |
| 10,854,332 | B2 | 12/2020 | Hamilton | |
| 10,915,605 | B2 | 2/2021 | Stadler | |
| 10,930,398 | B2 | 2/2021 | Jain | |
| 10,971,269 | B2 | 4/2021 | Kartoun | |
| 11,410,778 | B2* | 8/2022 | Ravindranathan | G16H 50/70 |
| 2010/0324936 | A1 | 12/2010 | Vishnubhatla | |
| 2011/0295621 | A1 | 12/2011 | Farooq | |
| 2015/0286784 | A1 | 10/2015 | Hagigi | |
| 2016/0019813 | A1 | 1/2016 | Mullen | |
| 2016/0042133 | A1 | 2/2016 | Sidel | |
| 2016/0235362 | A1 | 8/2016 | Lin | |
| 2016/0328993 | A1 | 11/2016 | Brogioli | |
| 2016/0378919 | A1* | 12/2016 | McNutt | G16H 40/63 705/3 |
| 2017/0046496 | A1 | 2/2017 | Johnstone | |
| 2017/0161469 | A1 | 6/2017 | Shibahara | |
| 2017/0245794 | A1 | 8/2017 | Sharma | |
| 2017/0262614 | A1* | 9/2017 | Vishnubhatla | G16H 50/20 |
| 2017/0271455 | A1* | 9/2017 | Tawara | H01L 21/30604 |
| 2017/0308981 | A1* | 10/2017 | Razavian | G16H 40/60 |
| 2018/0101659 | A1 | 4/2018 | Ninan | |
| 2018/0271455 | A1 | 9/2018 | Zhong | |
| 2019/0236465 | A1 | 8/2019 | Vleugels | |
| 2020/0258637 | A1 | 8/2020 | Jain | |

FOREIGN PATENT DOCUMENTS

| | | | | |
|---|---|---|---|---|
| WO | 2015081086 A1 | 6/2015 | | |
| WO | WO 2019/226576 A1 | * | 11/2019 | .............. A61B 5/00 |
| WO | WO 2021/021566 A1 | * | 2/2021 | ............. G06F 19/00 |

OTHER PUBLICATIONS

H. H. Nnuyen.; F. Mirza.; M. A. Naeem; M. Nguyen, A review on IoT healthcare applications and a vision for transforming sensor data into real-time clinical feedback (English), 2017 IEEE 21st Int. Conf. on Computer Supported Cooperative Work in Design (CSCWD) (2017, Page9s): 257-262), Apr. 1, 2017 (Year: 2017).*

Hristoskova, Anna; Sakkalis, Vangelis; Zacharioudakis, Giorgos; Tsiknakis, Manolis; De Turck, Filip, Onyology-Driven Monitoring of patient's vital Signs Enabling Personalized Medical Detection and Alert (English), Sensors (basel, Switzerland), 14(1), 1598-1628, Jan. 17, 2014 (Year: 2014).*

Ahmed, Zeeshan; Mohamed, Khalid; Zeeshan, Saman; Dong, XinQi, Artificial intellignce with multi-function machine learning platform development for better healthcare and precision medicine (English), Database: The journal of Biological Databases and Curation, 2020, baaa010, Mar. 17, 2020 (Year: 2020).

Parra-Calderon, Carlos Luis; Cahan, Amos; Mark, Roger; Sharafoddini, Anis; Dubin, Joel A; Lee, Joon, Patient Similarity in Prediction Models Based on Health Data: A Scoping Review (English), JMIR Medical Information, 5(1), e7, Mar. 3, 2017 (Year: 2017).

Rajkomar, A. and many others (see publication for other related people), Scalable and accurate deep learning with electronic health records (English), N P J Digital Medicine, 1, 18, May 8, 2018 (Year: 2018).

Aetna, Depression in Primary Care program, https://www.aetna.com/health-care-professionals/patient-care-programs/depression-primary-care-program.html; accessed as early as Sep. 9, 2019.

Anthem, https://www.anthem.com/wps/portal/ahpmedprovider?content_path=provider/oh/f3/s9/10/pw_ad076630.htm&rootLevel=2&label=Behavioral%20Health, accessed at least as early as Sep. 19, 2019.

CVShealth, CVS Health Introduces New Service to Help PBM Clients Manage Health and Wellness Benefit Solutions, Jun. 11, 2019; https://www.cvshealth.com/news-and-insights/press-releases/cvs-health-introduces-new-service-to-help-pbm-clients-manage.

Davison TE, McCabe MP, Mellor D. (2009) An examination of the "gold standard" diagnosis of major depression in aged-care settings. The American Journal of Geriatric Psychiatry, 17(5):359-67. doi: 10.1097/JGP.0b013e318190b901.

Eack, S. M., Greeno, C. G., & Lee, B. J. (2006). Limitations of the Patient Health Questionnaire in Identifying Anxiety and Depression: Many Cases Are Undetected. Research on social work practice, 16(6), 625-631. https://doi.org/10.1177/1049731506291582.

Optum, Behavioral Health, https://www.optum.com/content/dam/optum3/optum/en/resources/brochures/obh-overview-brochure-digital.pdf, accessed at least as early as Sep. 19, 2019.

Wahlbeck, K., Westman, J., Nordentoft, M., Gissler, M., & Laursen, T. (2011). Outcomes of Nordic mental health systems: Life expectancy of patients with mental disorders. British Journal of Psychiatry, 199(6), 453-458. doi: 10.1192/bjp.bp.110.085100.

* cited by examiner

MENTAL HEALTH PREDICTIVE MODEL MANAGEMENT SYSTEM

CROSS REFERENCE TO RELATED APPLICATIONS

This application claims priority to U.S. Provisional Patent Application Ser. No. 63/115,464, filed Nov. 18, 2020, which is hereby incorporated by reference and which the applicant claims benefit of priority under 35 U.S.C. § 119. This application also claims priority to and is a continuation-in-part of U.S. patent application Ser. No. 17/386,223, filed Jul. 27, 2021, which is hereby incorporated by reference and which the applicant claims benefit of priority under 35 U.S.C. § 120; said application Ser. No. 17/386,223 claims benefit of priority to U.S. Provisional Patent Application Ser. No. 63/115,464, filed Nov. 18, 2020.

TECHNICAL FIELD

Embodiments herein generally relate to digital cognitive behavioral therapy services. More specifically, but not by way of limitation, embodiments herein describe using predictive modeling in a mental health management system.

BACKGROUND

Recognizing, treating and supporting mental health issues requires an expansive treatment approach. For patients, the path to improvement is paved with expert guidance, treatment support, holistic care and more.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
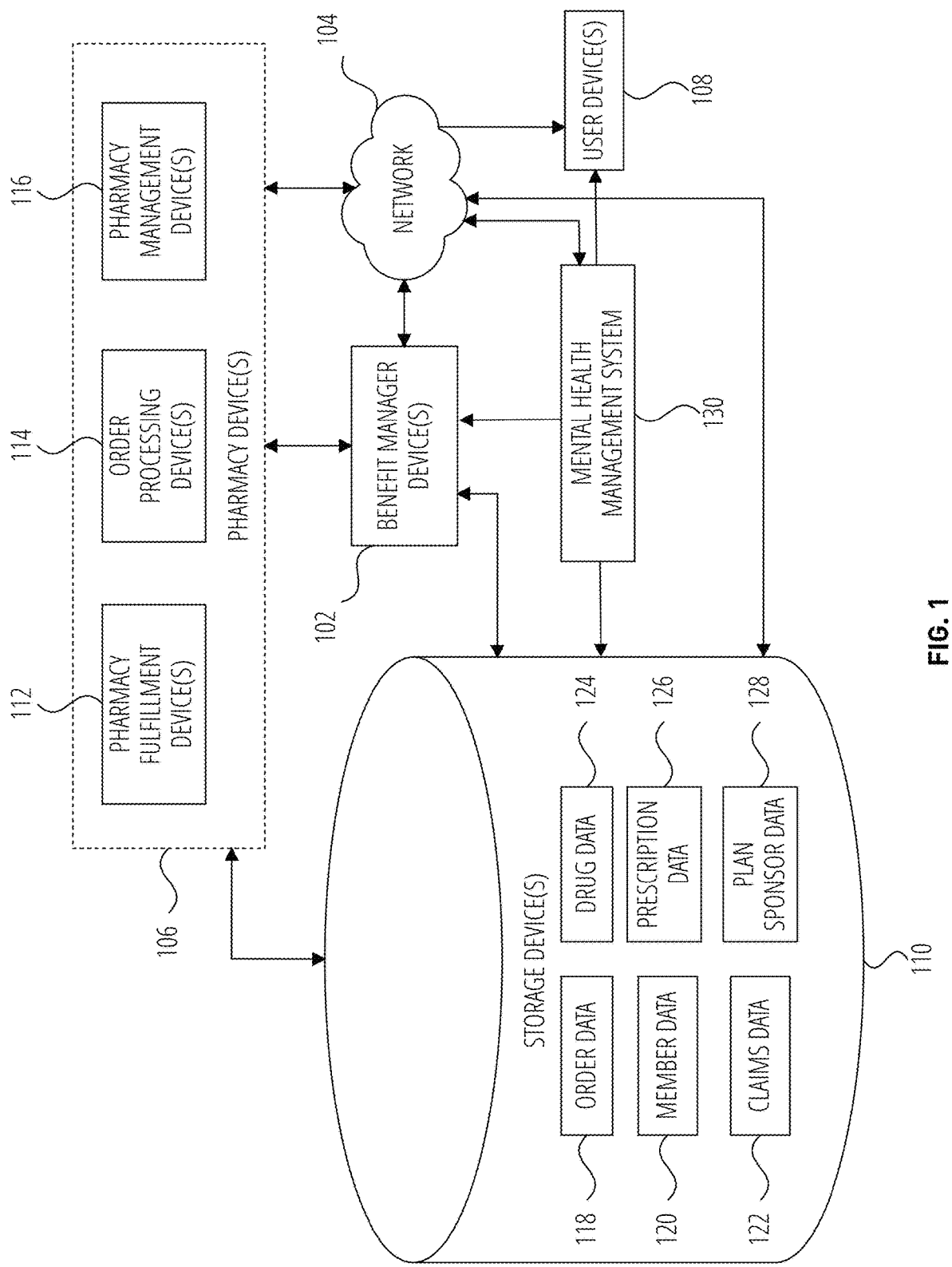
FIG. 1 is a block diagram of an example implementation of a system for a high-volume pharmacy, according to example embodiments.

Due to the nature of mental health, those with a mental illness or illnesses often live with their symptoms for long periods of time before seeking treatment, if they ever do so at all. In combination with predictive modeling, technologies related to digital cognitive behavioral therapy, education, awareness, caregiver support and telehealth support can help support patients struggling with those illnesses.

Embodiments herein describe a system for mental health care management using a combination of predictive modeling, health care provider outreach and digital cognitive behavioral therapy. Predicting disease state progression (based on pharmacy claims data records and/or medical claims data records) and providing needed support to prevent progression at an early point in a patient's mental health betterment journey can improve the overall quality of medical care. A mental health care management system may access patient data associated with a patient. The patient data may include demographic data, current medication data, historical medication data and other relevant patient data. The mental health care management system may determine, based on the patient data, the patient is associated with a trigger event.

In one example, the trigger event indicates that the patient is at risk for progression of their mental health illness. For example, based on the patient data, the mental health care management system may determine that the patient is someone who is at risk for progression of their depression, anxiety or insomnia.

In response to determining that the patient is someone who is at risk for progression of their mental health illness, the mental health care management system generates a prediction that the patient's current medication regiment will be modified with a second medication regimen within a predetermined amount of time (e.g., six months). In some examples, the prediction is generated using a machine learning model that is trained to analyze the patient data. In one embodiment, the second medication regimen may involve supplementing patient's current medication with a second medication that the patient is not currently using.

The mental health care management system may store the prediction in one or more databases and transmit that prediction to a health care provider (e.g., a pharmacist). For example, if the mental health care management system detects that a patient is highly likely to become a chronic user of an anxiety medication within the next six months, the mental health care system may transmit a notification that alerts the patient's health care provider. The mental health care system may further inform the patient's health care provider about counseling options to educate the patient on proper use of their medication. The mental health care system may also display to the patient's health care provider that the patient is eligible to enroll in digital cognitive behavioral therapy.

In another example, the trigger event indicates that the patient may benefit from further educational resources. For example, the mental health care management system may determine that the patient is new to therapy for an antidepressant medication. The mental health care management system may automatically send information to the patient about the anti-depressant medication (e.g., side effects, length of time required to see an effect, etc.). The send by the system can include generating a record that includes data specific to the individual patient. In some examples the information is automatically sent to a client device belonging to the patient. In some examples the information is stored in a secured record that can be accessed by the client device associated with the patient. In some examples the information is stored in a secured record at a server, which is held in behind a firewall and only notification about the information in the record is output with the information be held securely in the server.

In another example, the trigger event indicates that the patient may benefit from a follow-up from a pharmacist. For example, the mental health care management system may determine that the patient has not completed their entire course of medications and may transmit a notification to a pharmacist. For example, the notification may include information on how to contact the patient and educate them on the proper use of their medication. The notification can be a record or flag value in a record stored in the system.

In another example, the trigger event indicates that the patient may benefit from a follow up from the patient's health care provider. For example, a patient may be prescribed a medication indicative of a chronic disease and has a history of mental illness. The mental health care management system may, in response to the trigger event, send a notification to the patient's health care provider. For example, the notification may include information on the importance of screening, scheduling a medical follow-up with the patient and other relevant information about the patient's medication. The notification may be automatically generated by the mental health care management system and transmitted to a client device belonging to the patient's health care provider.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system may include a mental health management system 130 and a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication technical operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Virginia.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104. The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfillment device(s) 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order. The order data 118 can include mental health related medications, pain medication medications and data related thereto.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably. The member data can further include relationship of mental health prescriptions within the group of relationships stored in the member data.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

The mental health management system 130 enables a patient user using a patient device (e.g. user device(s) 108) to establish a communication session with a pharmacist associated with the pharmacy client (e.g., user device(s) 108) and a provider associated with the provider device (e.g., a user device(s) 108). During a communication session between the patient, and provider the mental health management system 130 identifies the patient using initial context data (e.g., the phone number the member is calling from, member account information, name, address, insurance information, information on spouse and dependents, etc.) and initiates a secure communication session.

Figure 4:
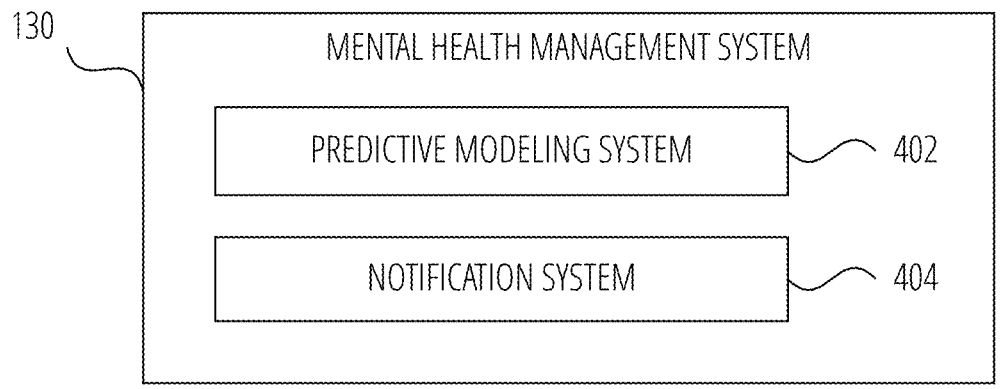
FIG. 4 is a block diagram of a predictive modeling system, according to example embodiments.

Further details of the mental health management system 130 are provided in relation to FIG. 4.

Figure 2:
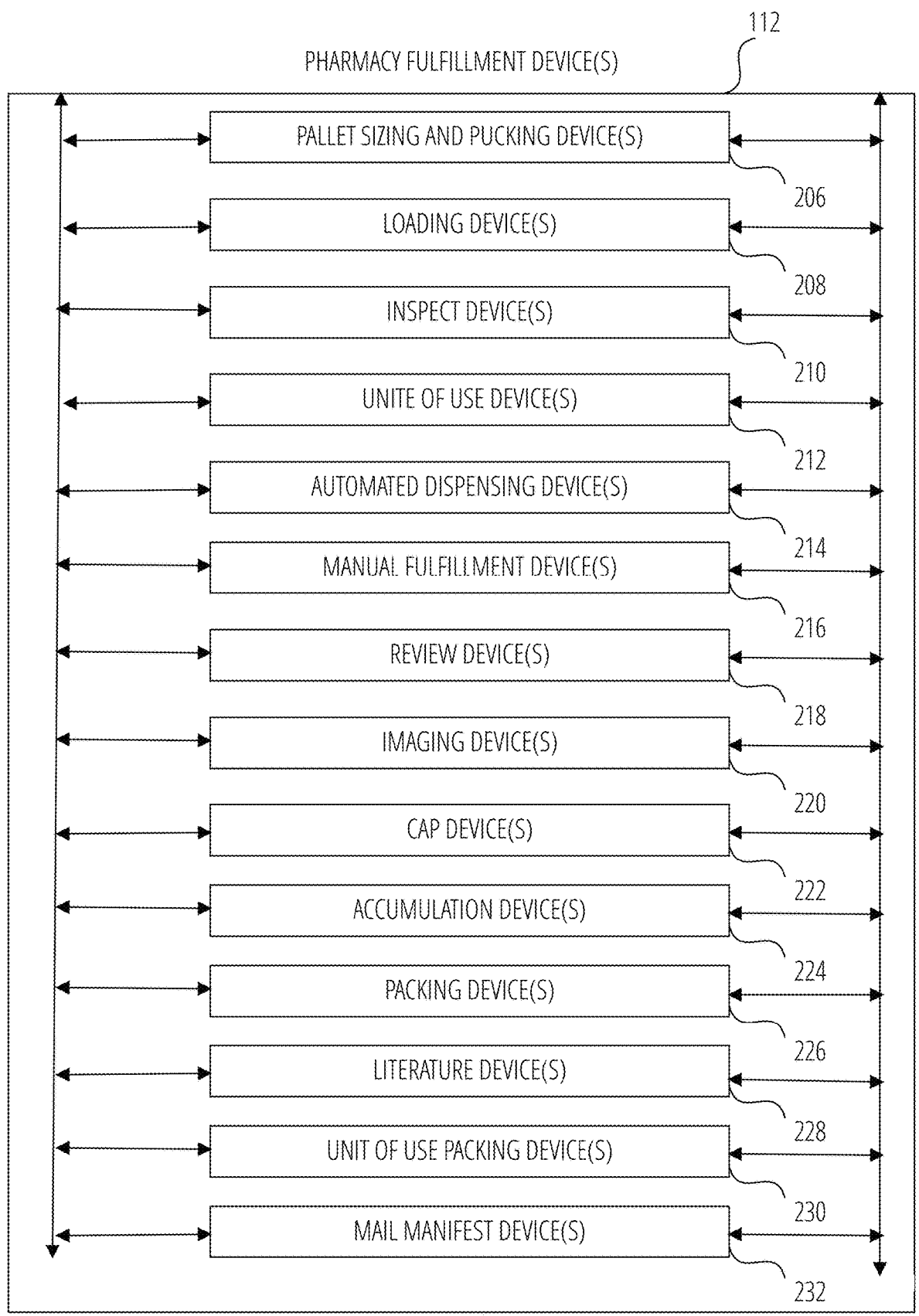
FIG. 2 illustrates a pharmacy fulfillment device, according to example embodiments.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck. In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
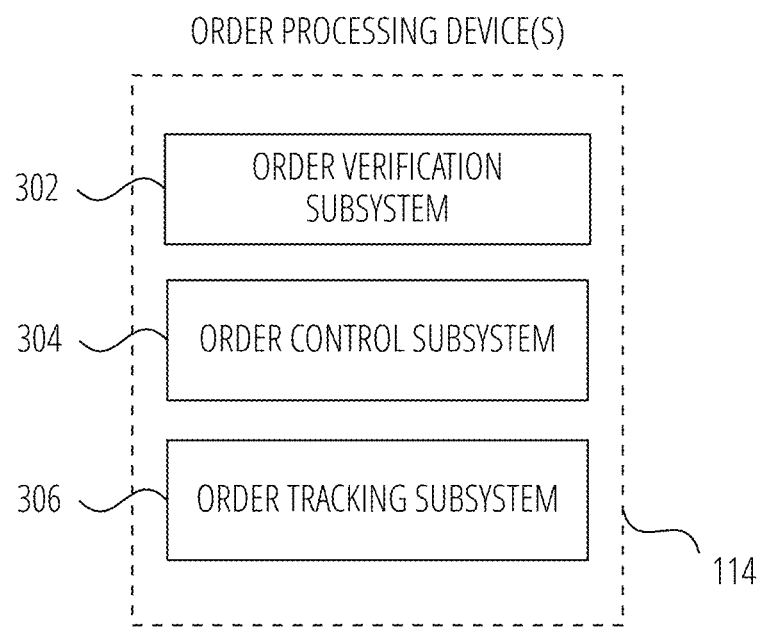
FIG. 3 illustrates an order processing device, according to example embodiments.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

FIG. 4 is a block diagram of a mental health management system 130, according to example embodiments. The mental health management system 130 in FIG. 4 includes a predictive modeling system 404 and a notification system 404. The mental health management system 130 can further include elements described with respect to FIG. 14 and FIG. 15 as a processor and memory, having instructions stored thereon, that when executed by the processor, causes the processor to control the functions of the mental health management system 130.

Figure 5:
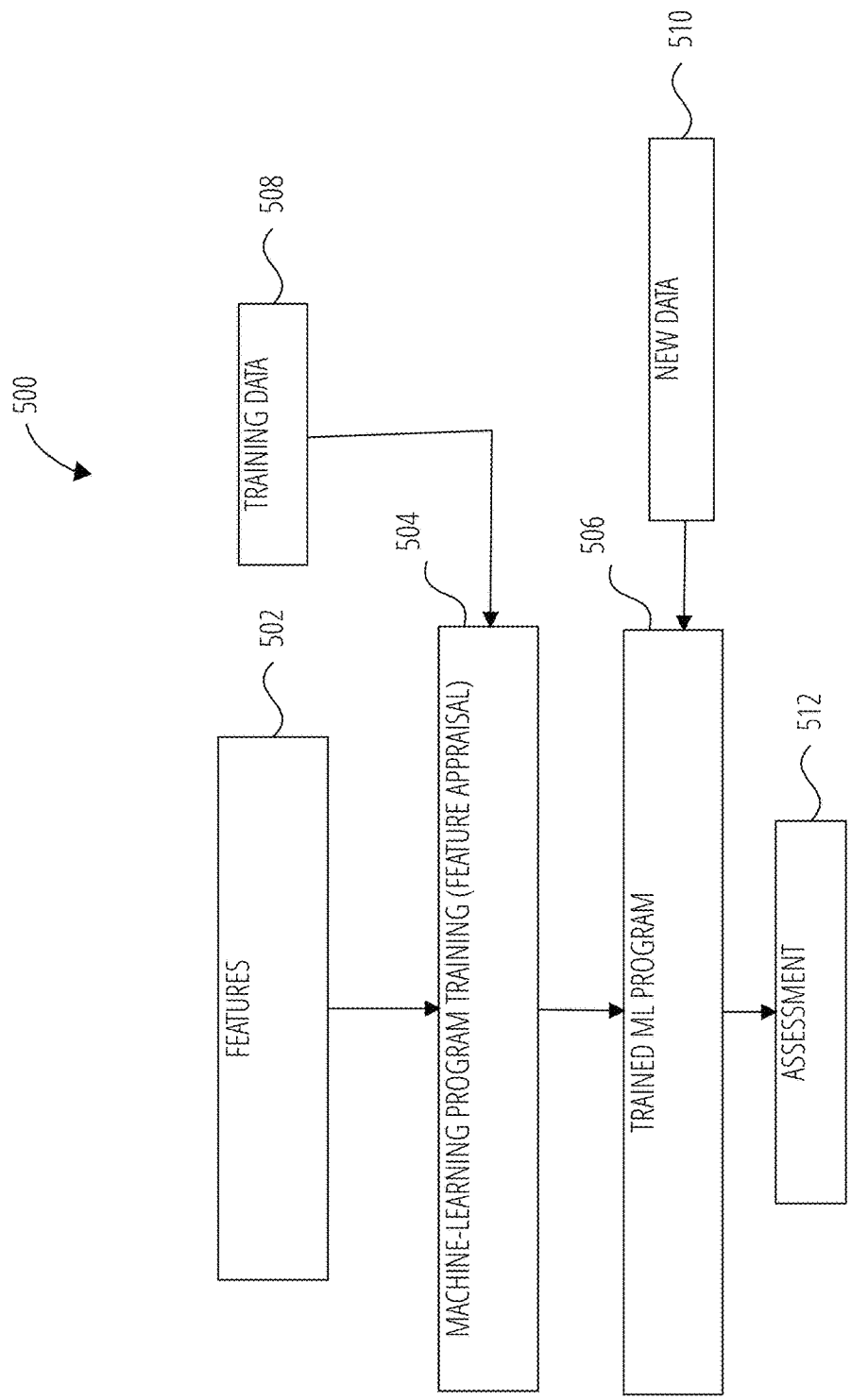
FIG. 5 illustrates the training and use of a machine-learning program, according to some example embodiments.

FIG. 5 illustrates the training and use of a machine-learning program, according to some example embodiments. In some example embodiments, machine-learning programs (MLPs), also referred to as machine-learning algorithms or tools, are utilized to perform operations associated with mental health prediction classification. Machine learning is a field of study that gives computers the ability to learn without being explicitly programmed. Machine learning explores the study and construction of algorithms, also referred to herein as tools, which may learn from existing data (e.g., medical care data, prescription data, other data, and combination thereof) and make predictions about new data. Such machine-learning tools operate by building a model from example training data 508 in order to make data-driven predictions or decisions expressed as outputs or assessment 512. Although example embodiments are presented with respect to a few machine-learning tools, the principles presented herein may be applied to other machine-learning tools.

In some example embodiments, different machine learning tools may be used. For example, Logistic Regression (LR), Naïve-Bayes, Random Forest (RF), neural networks (NN), matrix factorization, and Support Vector Machines (SVM) tools may be used for classifying or scoring medical health, mental health, the effect of drugs on a patient's health, or combinations thereof.

Two common types of problems in machine learning are classification problems and regression problems. Classification problems, also referred to as categorization problems, aim at classifying items into one of several category values (for example, is this object an apple or an orange? or is a prescription drug known to effect mental health or not?). Regression algorithms aim at quantifying some items (for example, by providing a value that is a real number). In some embodiments, example machine-learning algorithms provide a prediction probability that a patient may require an additional medication to be added to their treatment plan within a pre-determined time or a set time period. In some embodiments, example machine-learning algorithms provide a prediction probability (or score) that a patient may become chronic users of a medication. The machine-learning algorithms utilize the training data 508 to find correlations among identified features 502 that affect the outcome.

In an example, the identified features 502 can be generated from a data set that is first reduced by clinical data and ranges of data values in the reduced data set can also be set by the clinical data. The risk scores can be determined by predictive models that use only subsets of the data types available with the data set, e.g., prescription claims data, medical services data and the like. These clinical data reduction algorithm operates to reduce the data types, and, hence, the total data, which is reviewed to produce a predictive model that can produce a risk score for possible health risks, chance of addiction, or chance of severe side effects.

The machine-learning algorithms utilize features 502 for analyzing the data to generate an assessment 512. The features 502 are an individual measurable property of a phenomenon being observed. The concept of a feature is related to that of an explanatory variable used in statistical techniques such as linear regression. Features can be stored as type of data or the data itself. Choosing informative, discriminating, and independent features is important for effective operation of the MLP in pattern recognition, classification, and regression. Features may be of different types, such as numeric features, strings, and graphs. In an example embodiment, the features are those that assist in the prediction of a patient having an adverse progression or predicted progression in their treatment, e.g., based on the record of their prescription drugs.

The machine-learning algorithms utilize the training data 508 to find correlations among the identified features 502 that affect the outcome or assessment 512. In some example embodiments, the training data 508 includes labeled data, which is known data for one or more identified features 502 and one or more outcomes, such as detecting patients who may become chronic users of a medication.

With the training data 508 and the identified features 502, the machine learning tool is trained to generate a trained machine-learning program 506. The machine-learning tool appraises the value of the features 502 as they correlate to the training data 508. The result of the training is the trained machine-learning program 506.

The present systems and methods can use a processing system configured to: apply the predictive machine learning model to the reduced data set to generate the model. The predictive machine learning model is trained using at least one of a) a k-nearest neighbor algorithm, b) a logistic regression algorithm, c) a random forest algorithm, and d) a naïve Bayesian algorithm. The k-nearest neighbor algorithm can be configured to consider a set of neighbors comprising the nearest twenty neighbors identified for each of the plurality of leaves of the tree-structure.

When the feature change or the feature values changes. e.g., based on clinical data, the predictive model can be re-trained.

The machine learning systems are used identify characteristics or features associated with reduced data sets, where the characteristics have relationships to the data sets that are unknown and unpredictable without the use of the disclosed machine learning systems. The field further relates to the use of such machine learning systems in therapies that may have a high rate of undesired affects, such as mental health, if not timely identified, where the machine learning systems and methods generate predictive models that determine whether a given patient or features relating to a patient in the reduced data set predict a possible adverse effect.

Figure 6:
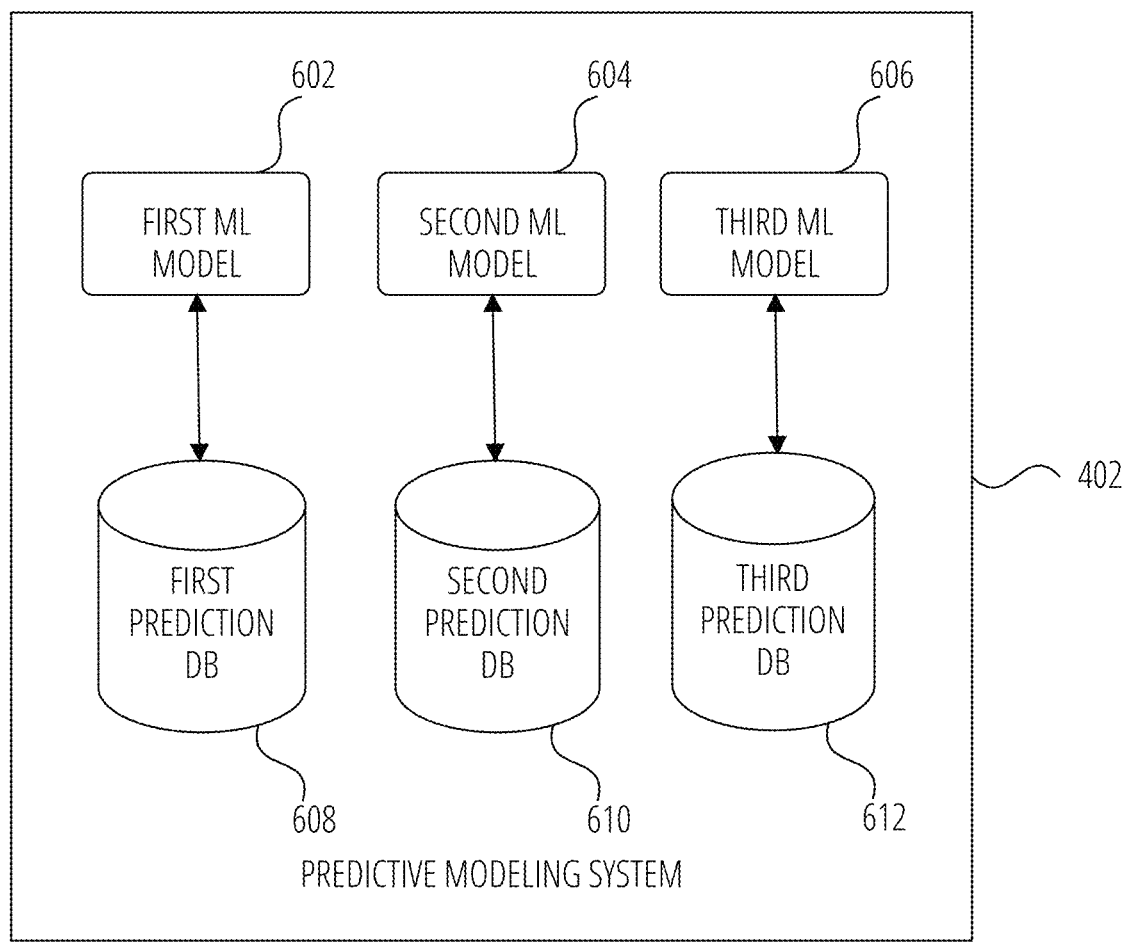
FIG. 6 is a block diagram of a predictive modeling system 402, according to some example embodiments.

FIG. 6 is a block diagram of a predictive modeling system 402, according to some example embodiments. The predictive modeling system 402 is shown to include a first machine learning model 602, a first prediction database 608, a second machine learning model 604, a second prediction database 610, a third machine learning model 606, and a third prediction database 612.

The first machine learning model 602, second machine learning model 604 and third machine learning model 606 are each machine learning models trained to analyze data and generate a prediction based on the analysis.

The first machine learning model 602 may be a machine learning model that is trained to generate a prediction that a patient will require a second medication to be added to their treatment plan within a predetermined time frame or set time period (e.g., three months, six months, one year plus or minus two months). For example, if a patient is currently taking a current medication (e.g., antidepressants), the first machine learning model 602 will generate a prediction that that patient will also be taking a second medication to augment the efficacy of the antidepressant within the set time period, e.g., in the next six months. In an example embodiment, the drugs and treatments used to generate predictive models are directed to mental health issues. The first machine learning model 602 may be trained on aspects of member data 120 and aspects of claims data 122 (prescription data, medical data, or combination thereof). The aspects of member data 120 may include demographic information about the patient (e.g., age, gender, weight, etc.), current list of medication that the patient is taking, or the patient's medical history (e.g., mental health illness history). The aspects of claims data 122 may include information about the patient's current and previous prescriptions such as number of prescriptions the patient currently has, the average number of days between prescription refills for a current medication (or previous medication), number of days between the end of a first prescription and the beginning of a second prescription (e.g., for the same medication or different medication), etc.

The first machine learning model 602 receives new patient data as input and outputs a prediction that the patient will require a second medication to be added to their treatment plan within a predetermined time frame or a set time period. The prediction is stored in the first prediction database 608. The prediction can be a percentage value that the patient will require the second medication. In an example embodiment, the prediction value is a numerical score or a binary score indicating that the patient is likely to require the second medication. In an example, the prediction is normalized score relative to other patients.

The second machine learning model 604 may be a machine learning model that is trained to generate a prediction that a patient will become a chronic user of a second type of medicine within a predetermined time frame (e.g., six months) or a set time period. For example, if a patient is struggling with insomnia and taking medication to treat insomnia, the second machine learning model 604 may generate a prediction that that patient will become a chronic user of their insomnia medication. The prediction can be a percentage value that the patient will become a chronic user of the second medication. In an example embodiment, the prediction value is a numerical score or a binary score indicating that the patient is likely to become a chronic user of the second medication. In an example, the prediction is normalized score relative to other patients in general or patients who take the second medication.

The second machine learning model 604 may be trained on aspects of member data 120 and aspects of claims data 122. The aspects of member data 120 may include demographic information about the patient (e.g., age, gender, weight, etc.), residence address, minimum age of members in a household, etc. The aspects of claims data 122 may include the number of days since the first prescription claim, the number of extra pills between the day when the patient runs of total supply to their next prescription refill, number of prescription refills, etc.

The second machine learning model 604 receives new patient data as input and outputs a prediction that the patient will become a chronic user of insomnia medication within a predetermined timeframe or set time period. The prediction is stored in the second prediction database 610.

The third machine learning model 606 may be a machine learning model that is trained to generate a prediction that a patient will become a chronic user of a third type of medication within a predetermined time frame (e.g., six months) or set time period. For example, if a patient is struggling with anxiety and taking medication to treat anxiety, the third machine learning model 606 may generate a prediction that that patient will become a chronic user of their anxiety medication. The prediction can be a percentage value that the patient will become a chronic user of the anxiety medication. In an example embodiment, the prediction value is a numerical score or a binary score indicating that the patient is likely to become a chronic user of the anxiety medication. In an example, the prediction is normalized score relative to other patients in general or patients who take the anxiety medication. The third machine learning model 606 may be trained on aspects of member data 120 and aspects of claims data 122. The aspects of member data 120 may include demographic information about the patient (e.g., age, gender, weight, etc.), residence address, minimum age of members in a household, etc. The aspects of claims data 122 may include the number of days since the first prescription claim, a medication possession ratio (e.g., percentage of time a patient has access to medication), number of days supply for anxiety medication claims, etc.

The third machine learning model 606 receives new patient data as input and outputs a prediction that the patient will become a chronic user of anxiety medication within a predetermined timeframe. The prediction is stored in the third prediction database 612.

Figure 7:
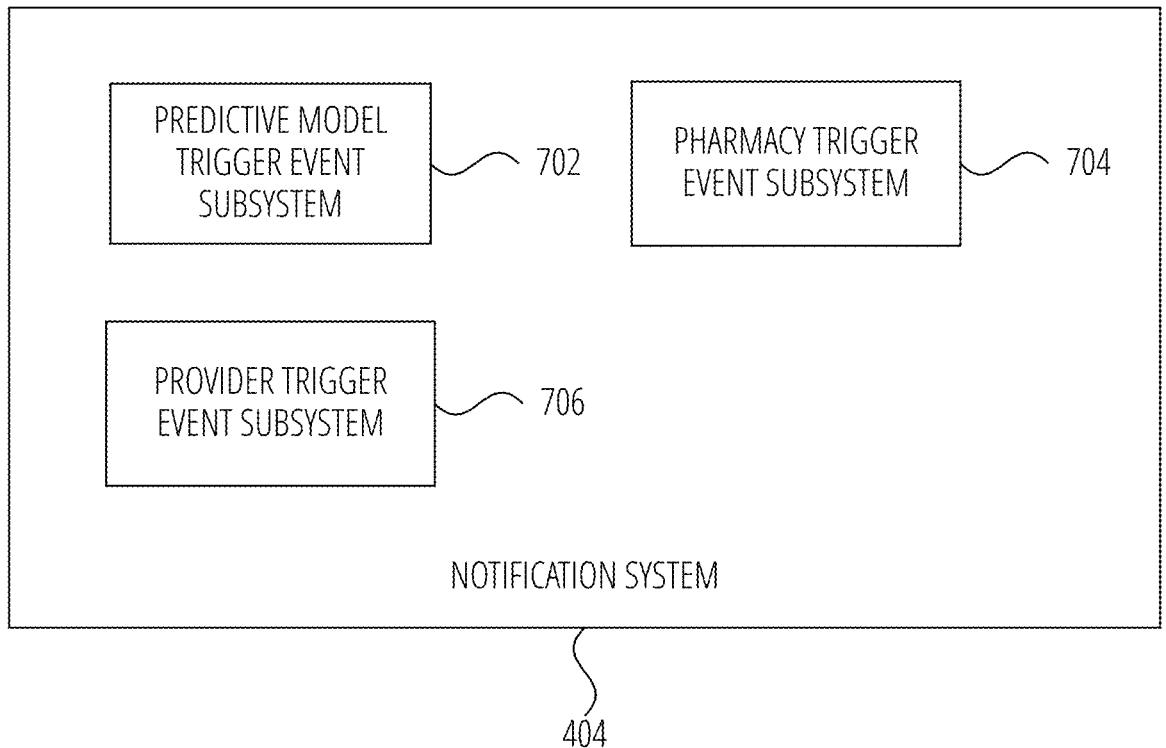
FIG. 7 is a block diagram of a notification system, according to example embodiments.

FIG. 7 is a block diagram of a notification system 404, according to example embodiments. The notification system 404 is shown to include a predictive model trigger event subsystem 702, a pharmacy trigger event subsystem 704, and a provider trigger event subsystem 706.

The predictive model trigger event subsystem 702 may store a first list of trigger events and associated trigger responses. Trigger events may be defined based on one or more of member data 120 or claims data 122 associated with a particular patient. The first list of trigger events may indicate that the patient is at risk for progression of their mental health illness (e.g., depression, anxiety, or insomnia). The predictive model trigger event subsystem 702 may generate notifications (e.g., based on the associated trigger response) to a benefit manager device 102 or a pharmacy device 106. The predictive model trigger event subsystem 702 may flag a record in a database that relates to the notification such that a defined notification, e.g., an electronic message, is selected to be sent from and stored in the predictive model trigger event subsystem 702. The flag control the loading of instructions for tasks to be performed in the system.

The pharmacy trigger event subsystem 704 may store a second list of trigger events and associated trigger responses. The trigger events may be defined based on one or more of member data 120 or claims data 122 associated with a particular patient. The second list of trigger events may indicate that the patient may benefit from follow up from a pharmacist. For example, the pharmacy trigger event subsystem 704 may have a trigger event that indicates a patient has filled a prescription for a medication (e.g., an antidepressant) but did not refill that prescription. The associated trigger response may include one or more of prompting a pharmacist to call the patient, ask about reasons for discontinuation, or educate the patient on proper use of their medication. The pharmacy trigger event subsystem 704 may generate a notification describing the associated trigger response and transmit the notification to the benefit manager device 102 and/or the pharmacy device(s) 106. The notification may be an alert within an application (e.g., a mobile or web application including the mental health management system 130). The notification may be displayed on a graphical user interface (GUI) of the benefit manager device 102 and/or the pharmacy device(s) 106. The pharmacy trigger event subsystem 704 may have a trigger event that indicates a patient is currently taking a first medication and has been prescribed a second medication that may have properties that interact with the first medication. The associated second trigger response may include one or more of calling a patient or sending the patient information on the risks of taking both medications concurrently.

The provider trigger event subsystem 706 may store a third list of trigger events and associated trigger responses. In some examples, the third list of trigger events and associated trigger responses includes at least a portion of trigger events from the second list described above. The third list of trigger events may indicate that the patient may benefit from a follow up from a provider.

For example, the pharmacy trigger event subsystem 704 may have a first trigger event that indicates that a patient is new to taking a medication. The associated trigger response may also include a provider trigger which would prompt the physician that the patient may be a candidate for digital cognitive behavioral therapy, to indicate the importance of screening the patient for a mental health condition, reminder to inform the patient on side effects of the medication, scheduling follow-ups with the patient to adjust the dose/regimen as needed, etc. The provider trigger event subsystem 706 may generate a notification describing the associated trigger response and transmit the notification to the benefit manager device(s) 102 and/or the pharmacy device(s) 106.

The provider trigger event subsystem 706 may have a second trigger event that indicates that a patient is approaching six months of continued use of a medication. The associated trigger response may be alerting the provider that the physician needs to authorize any further use of the medication at the six-month mark. The provider trigger event subsystem 706 may further have a third trigger event that indicates that a patient is receiving similar medications or having dose changes from different providers. The associated trigger response may alert the provider of those changes. In some examples, the provider trigger event subsystem 706 may have a fourth trigger event that indicates that a patient has received a medication indicative of a chronic disease and the patient has a history of mental health illness. The associated trigger may alert the provider of the patient's medical history.

Predictive Modeling System

Figure 8:
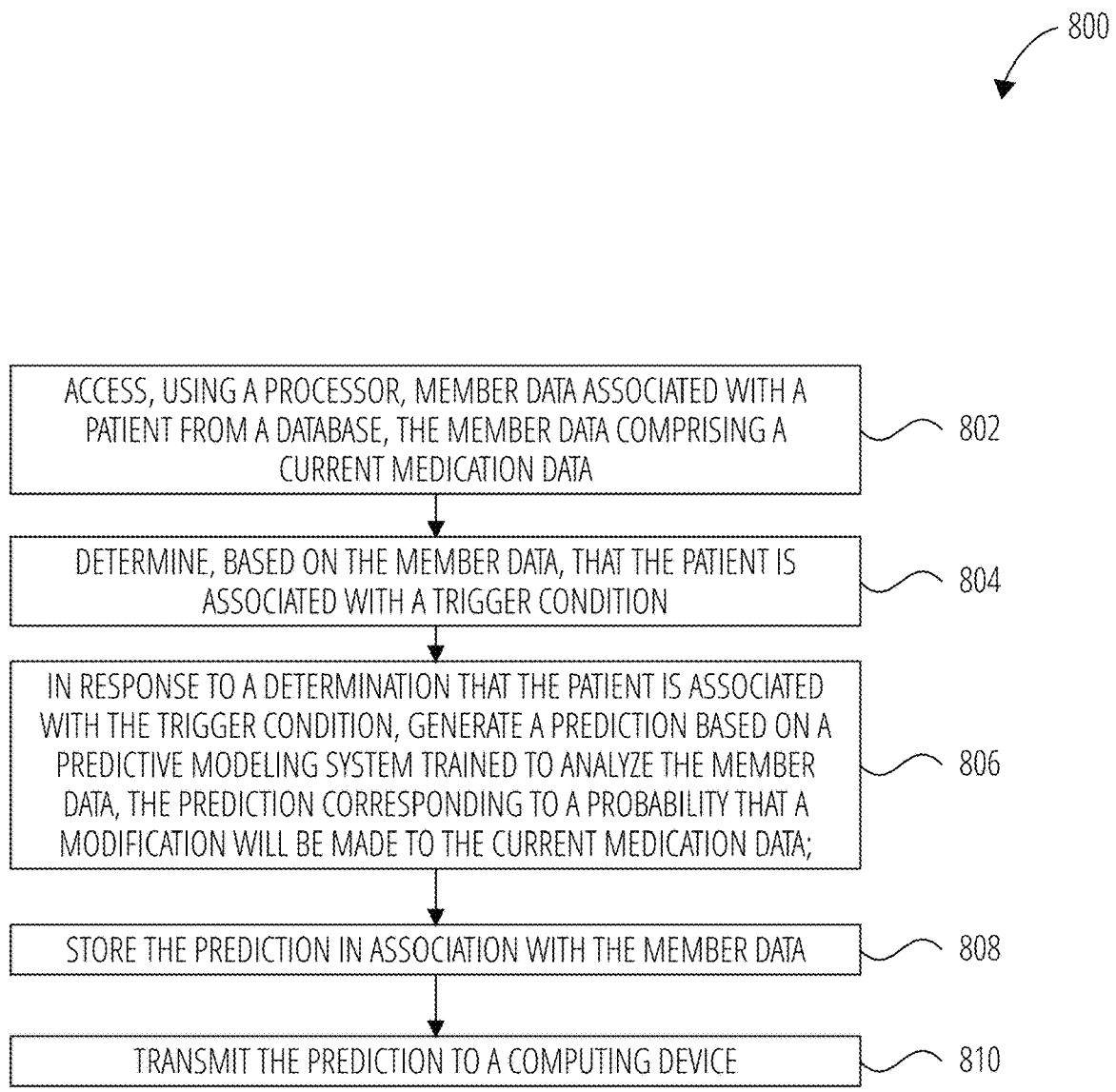
FIG. 8 is a flowchart of a method for improving a mental health illness treatment plan by a mental health management system, according to example embodiments.

FIG. 8 is a flowchart of a method for improving a mental health illness treatment plan by a mental health management system, according to example embodiments. The method 800 can be performed by the mental health management system 130 in FIG. 1. In an embodiment, a processor (or circuitry dedicated to performing instructed tasks) included in the mental health management system 130 performs the method 800 or causes the mental health management system 130 to perform the method 800 or portions thereof.

At operation 802, the mental health management system 130 accesses, using a processor, member data associated with a patient from a database. For example, the member data may be the member data 120. The member data may comprise a current medication data. For example, the current medication data may be a first medication that the patient is currently taking.

At operation 804, the mental health management system 130 determines, based on the member data, that the patient is associated with a trigger event. The trigger event may be one or more events of the first list of trigger events described in connection with FIG. 6. The trigger event may trigger any of the predictive models described herein. The predictive model trigger event subsystem 702 may perform operation 804. In some examples, prior to performing operation 804, the mental health management system 130 validates the member data using one or more aspects of the member data 120 or the claims data 122. For example, prior to performing operation 804, the mental health management system 130 may determine one or more of the following: the patient has been using a medication for a predetermined amount of time, the patient is within a high-risk age group, the patient has a mental health illness history, the patient has had a new prescription added to their treatment plan within the past year, the patient has a minimum number of prescription claims for a specific type of medication, the patient has been continuously refilling their prescription for their current medication for a minimum number of days, etc. It is to be understood than any aspect of the member data 120 or claims data 122, or combination thereof may be used to validate the patient data. The validation may be used to ensure an accurate prediction from the predictive modeling system 402. In some examples, if the patient does not pass the validation process, the mental health management system 130 generates an alert that the patient does not meet the requirements for analysis using the predictive modeling system 402. The alert may be transmitted to one or more of the benefit manager device 102 or the pharmacy device 106.

At operation 806, in response to a determination that the patient is associated with the trigger event, the mental health management system 130 generates a prediction based on a predictive modeling system trained to analyze the member data. The prediction corresponds to a probability that a modification will be made to the current medication data. In some examples the prediction corresponds to a probability that the patient's current medication data will be modified with a second medication data within a predetermined amount of time. In an example, for a first predictive model, adding a medication to an existing treatment regimen would be a modification. In another example, if a modification can be changing a same medication as needed and then the treatment regimen changes to take the same drug, with or without additional drugs, chronically. The predictive modeling system may be a machine learning model from the predictive modeling system 402. For example, the machine learning model may be the first machine learning model 602. In some examples the second medication data is indicative of a second medication that is different from the first medication.

In some examples, the machine learning model is the second machine learning model 604. The second medication data may be indicative of extended use of the current medication (e.g., indicative of chronic usage of insomnia medication).

In some examples, the machine learning model is the third machine learning model 606. The second medication data may be indicative of extended use of the current medication (e.g., indicative of chronic usage of anxiety medication).

At operation 808, the mental health management system 130 stores the prediction in association with the member data. At operation 810, the mental health management system 130 transmits the prediction to a computing device. The computing device may be any of the user device(s) 108, benefit manager device(s) 102, or pharmacy device(s) 106. In some examples the mental health management system 130 causes display of the prediction as a notification on the computing device.

Example Use Cases—Predictive Modeling System

Figure 9:
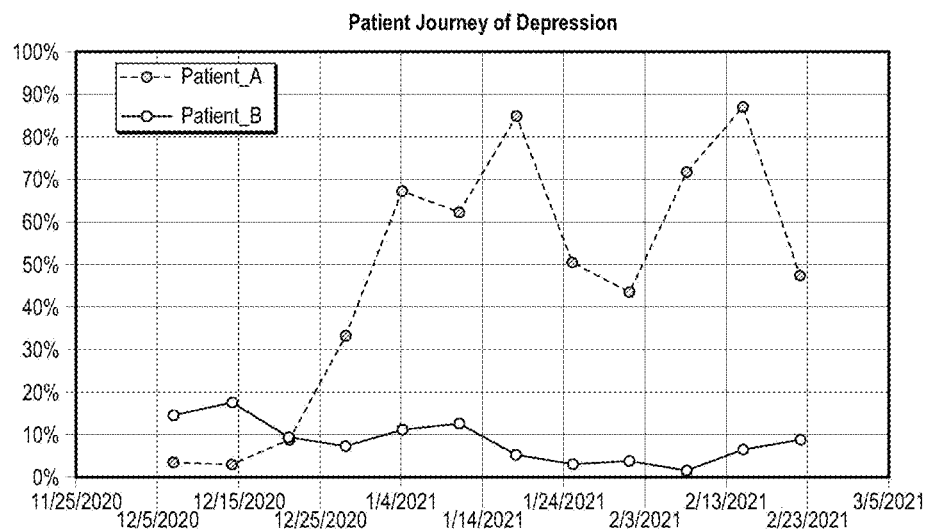
FIGS. 9-11 are example use cases for a predictive modeling system, according to some example embodiments.
Figure 10:
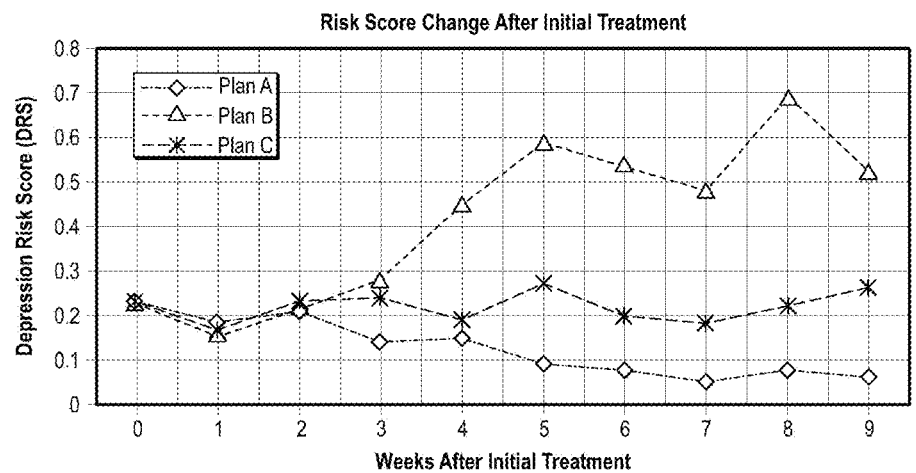
Figure 11:
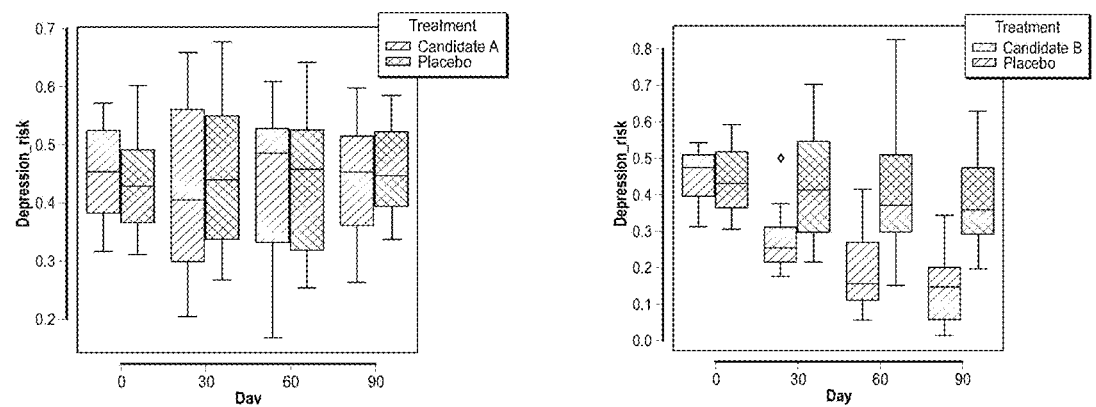

FIGS. 9-11 are example use cases for a predictive modeling system 402, according to example embodiments. The predictive modeling system 402 generates a probability that a patient's current medication regimen will be updated with a second medication regimen, within a predetermined time. The probability generated by the predictive modeling system 402 may be referred to herein as a "mental health risk score."

The mental health risk score may be used by clinical providers or health care providers (e.g., physicians, therapists and the like) as a clinical reference to help them better optimize treatment strategy. Leveraging the predictive modeling system 402 provides clinical providers with a quantitative evaluation of mental health issue progressions, which can in turn help physicians or pharmacists identify optimized treatment strategy earlier on. The pharmacists can be informed of the medical risk score by electronic communication to a pharmacist device, which can be remote from the system generating the score. In an example, a flag in the records in the server of the system can trigger a communication to the pharmacist device, which can indicate a level of the risk, relative risk or absolute risk score. Likewise, medical providers, e.g., physicians, can be informed of the risk score on their provider devices.

The predictive models that can produce the risk score can include features found in data about patients treated or not being treated for certain illnesses, e.g., mental health such as depression, insomnia, anxiety or the like. Features that can be identified and used by the machine learning can include therapies, drug group, modeling population, behaviors to predict, unit of prediction, patient drug group selection period, index period, look back periods, follow up period, eligibility, age and exclusions. These features and a first pass of all the possible values of the features in the medical database can be set based on analysis of the clinical data. This reduces the quantity of data and provides a data training set for the machine learning execution. For example, based on the type of treatment, e.g., one of depression, insomnia, anxiety or other, the ranges of values for each of the features can be set based on clinical data. The machine learning system can act on the defined reduced data set. In an example embodiment, the index period can be set to one month, two months, three months or up to 270 days. In an example embodiment, the look back period can be set to one month, two months, three months or up to 270 days, or in a range of ninety days to one hundred eighty days, or one year or less. In an example embodiment, the follow up period can be set to one month, two months, three months or up to 270 days, or in a range of ninety days to one hundred eighty days, or one year or less. The exclusions can be based on addition of additional prescription medications or diagnosis for a patient. The clinical analysis system can operate to set these values. Additional examples of incorporating data for disease management care that can be used in the present model are described in U.S. Pat. No. 8,799,030, which is hereby incorporated by reference. Additional examples of processing data for generating data sets for predictive modeling are described in U.S. Pat. No. 10,649,983, which is hereby incorporated by reference.

FIG. 9 is an illustration of the change over time of two patients' mental health risk scores. Specifically, the illustration depicts two patients' journey of depression. In FIG. 9, Patient A has a much higher mental health risk score after two weeks, compared to Patient B. Once a mental health risk score is in the 80th percentile range or increases over four times within 30 days and is above the 50th percentile range, the mental health management system 130 may trigger a notification to alert the patient's clinical provider, health insurance provider, and/or pharmacist. The notification may indicate that special attention is required on the patient's current medication regiment. The exact parameters of the notification triggering system (e.g., controlled by the notification system 404) may be tuned based on exact clinical requirements with such requirements being different for different patient demographics.

FIG. 10 is an illustration of the change over time of a patient's mental health risk score (e.g., depression risk score) based on three treatment plans directed towards a patient diagnosed with depression. In one example, if the depression risk score of a patient increases by 50% after 30 days of treatments or exceeds the 50th percentile risk score, the mental health management system 130 triggers an alert and a notification is sent to a clinical provider (e.g., specialist, psychiatrist) responsible for providing prior diagnosis on this patient. The notification may indicate that the mental health status of this patient is still progressing and needs specific attention. The notification may be an email, a phone call, or any suitable form of communication with the provider. With this type of alert, the clinical provider will be able to consider switching their treatment strategy on that patient as early as 30 days after the initial diagnosis. It is to be understood that the parameters of the alerts and notifications may be adjusted by a patient, a clinical provider, or both.

In one example, the mental health risk score can be used to generate a standard score used to evaluate the treatment efficiency of psychiatrists. For example, the mental health management system 130 may capture changes in patients' risk score before and after treatments (60 days after initial diagnosis/treatment). The changes in the patients' risk scores may be aggregated on the physician level. For example, median mental health risk score changes at a physician level are collected (e.g., median health risk score changes corresponding to a particular physician) and normalized. The final standard score may fall within a range 0-10, with a median score of 5.

The mental health management system 130 can incorporate data such as a physician's number of years of experience, patient ratings of a physician, specialty fields of the physician, and the cost/affordability of the physician. This will improve the mental health management system 130 by providing high quality and detailed information to help patients pick their desired physicians and greatly enhance the transparency of the care system. The standard also provides additional information in terms of treatment efficiency as a reference to health plan providers with regards to helping with negotiating contracts with health centers and including psychiatrists and/or health centers into their health care networks.

In one example, the mental health risk score may be used as one of the attributes in cost prediction for health care costs such as life insurance costs. Traditionally, health insurance companies forecast overall health care costs in the future for businesses based on their respective employees' demographic and health information before proposing prices for the next year and negotiating the contracts. Similarly, much of this information, such as prescription data, medical history data, and credit score histories have been leveraged by life insurance companies to calculate life insurance costs for customers. The mental health risk score can be added to this list of raw attributes and bring differential values to both parties. The introduction of mental health risk scores into both domains will greatly improve the accuracy of predictions.

FIG. 11 is an illustration of changes in patients' mental health risk score treated by two different drug candidates (A and B) over a 90-day period. The mental health risk score may be used to provide an alternative reference standard to monitor mental health diseases progression for drug development. Currently, there are no biomarkers to measure or monitor the level or progression of mental health diseases objectively. The mental health risk scores may be used as an alternative reference or 'biomarker' to monitor the clinical performance of drug candidates and provide information for patient grouping, improving the success rate of drug development especially when pharmaceutical companies decide to continue or discontinue work on specific drug candidates. The mental health risk score (e.g., Depression Risk Score (DRS) may be leveraged as an essential criterion to enroll appropriate patients for drug trials. As illustrated in FIG. 11, only patients with a risk score between 0.3-0.6 are selected for drug trials (treatment and placebo group). The drug candidate A has not been able to impact the progression of the mental health condition (e.g., depression) significantly, therefore it is likely not effective in treating depression. In comparison, the drug candidate B significantly reduced the progression of depression. Therefore, drug candidate B is likely a good candidate for depression treatment.

Notification System

Figure 12:
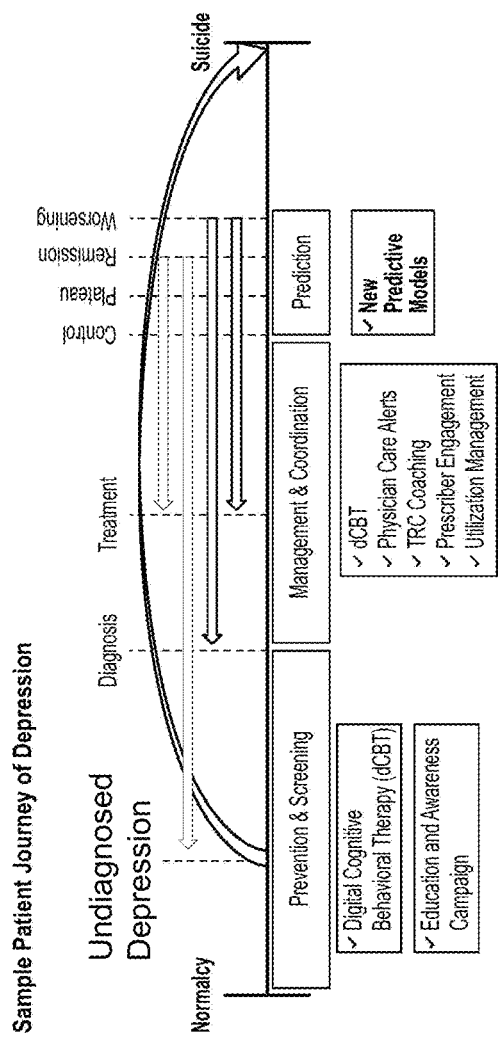
FIG. 12 is an illustration of a patient's journey through mental illness and corresponding treatment solutions, according to example embodiments.

FIG. 12 is an illustration of a patient's journey through mental illness and corresponding treatment solutions. The mental health management system 130 provides an integrated solution to enable the synergies among the predictive modeling system 402 and the notification system 404. The predictive modeling system 402 provides machine learning model predictions aimed to describe a probability that a patient's current medication regimen will be modified with a second medication regiment. The notification system 404 provides automated outreach mechanisms that allow physicians, pharmacies, health care providers and patients to communicate and facilitate treatment. For example, the digital behavioral cognitive therapy (dCBT) and education and awareness campaigns may be generated as part of the notification system 404 to aid in prevention and screening of mental health issues of a patient. The dCBT, Physician Care Alerts, Therapeutic Resource Center (TRC) coaching, prescriber engagement and utilization management may be generated as part of the notification system 404 to aid in management and coordination of a patient's mental health issue. Thus, in combination, the predictive modeling system 402 and the notification system 404 work together to provide real-time individualized solutions for patients.

FIG. 12 shows that the model can predict various states of treatment, e.g., control, plateau, remission and worsening. The management and coordination can be a basis for treatment and diagnosis, will triggering therapy, provider care alerts, care center coaching, prescriber engagement and utilization management. The model can also trigger prevention and screening, which can be used to prevent severe events and move patients toward normalcy. Remission may result in new treatment or undiagnosed depression.

While FIG. 12 shows that the remission feeds into the treatment phase, remission can also feed to normalcy. In another example, there is no connection between the remission and treatment. Not all patient members will experience each of these steps or treatment flows, actual or predicted, as shown in FIG. 12.

The generation of the flags in records can trigger campaigns to propose mental health or other health solutions. Some health programs can be delivered electronically through third party software, which can be part of the health program. The generated flags can start communications to members inviting them to participate in the health program, e.g., dCBT therapy. Some communications can be independent of the triggering flags. Members are also told about dCBT during the pharmacist outreaches, who may have received a communication from the system.

Figure 13:
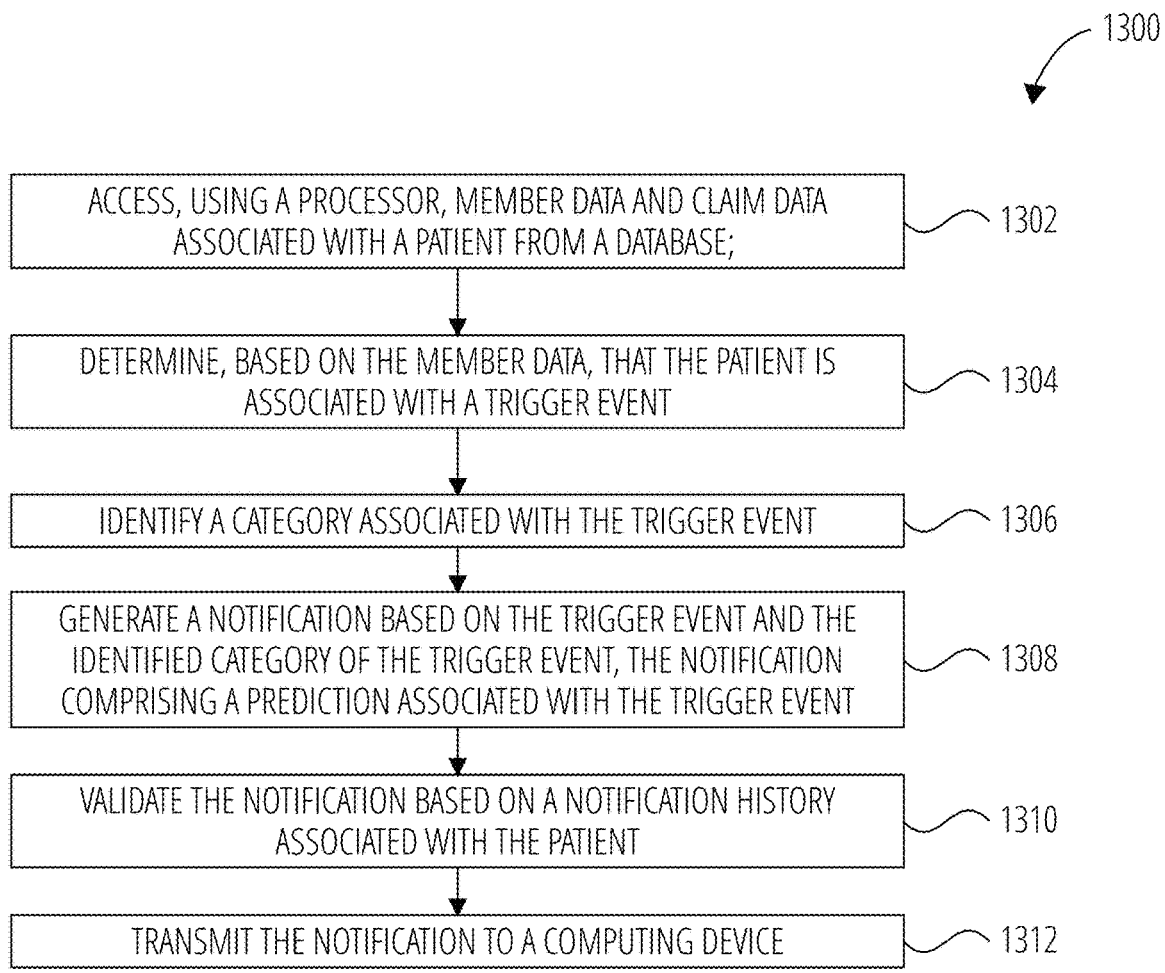
FIG. 13 is a flowchart of a method for improving a mental health illness treatment plan by a mental health management system, according to example embodiments.

FIG. 13 is a flowchart of a method for improving a mental health illness treatment plan by a mental health management system, according to example embodiments. The method 1300 can be performed by the mental health management system 130 in FIG. 1. In one embodiment, a processor (or circuitry dedicated to performing instructed tasks) included in the mental health management system 130 performs the method 1300 or causes the mental health management system 130 to perform the method 1300.

At operation 1302, the mental health management system 130 accesses, using a processor, member data and claim data associated with a patient from a database. For example, the member data may comprise a current medication data. At operation 1304, the mental health management system 130 determines, based on the member data, that the patient is associated with a trigger event. The trigger event may be the any of the trigger events described in relation to FIG. 7. At operation 1306, the mental health management system 130 identifies a category associated with the trigger event. For example, the category may indicate that the trigger event is associated with the predictive model trigger event subsystem 702, the pharmacy trigger event subsystem 704, or the provider trigger event subsystem 706. In some examples, a trigger event may be associated with multiple categories.

At operation 1308, the mental health management system 130 generates a notification based on the trigger event and the identified category of the trigger event. The notification may be generated by the notification system 404. In some examples, the notification comprising a prediction associated with the trigger event. For example, the prediction may be the prediction generated by the predictive modeling system 402. Further details of the prediction may be found in connection with FIG. 8.

At operation 1310, the mental health management system 130 validates the notification based on a notification history associated with the patient. For example, if a patient is above 18 years old and is on an anti-depressant, anti-anxiety or anti-insomnia medication, a notification will be sent each month towards the middle of the month for a period of 12 weeks. In another example, if a patient is new to therapy or new to a pre-defined type of medication, a notification will be sent once a year. In another example, if the patient beings a new modification or does not refill a prescription, a notification may be triggered once.

Once a notification is sent via the notification system 404, the mental health management system 130 stores an indication of the transmittal of the notification in association with a notification history associated with the patient. The notification history may be stored in one or more databases (e.g., member data 120, claims data 122, order data 118, prescription data 126, etc.). In operation 1312, the mental health management system 130 transmits the notification to a computing device. The computing device may be any of the user device(s) 108, Pharmacy Device(s) 106, or benefit manager device(s) 102.

Example Use Cases—Notification System

In one example, the notification system 404 is used to connect clinical providers (e.g., physicians) with prediction results of the predictive modeling system 402. Leveraging the insights of prediction risk from mental health models provide a quantitative evaluation of a patient's mental health issue progression, which can help physicians to identify optimized treatment strategy early.

In another example, the notification system 404 is used to expand the machine learning models associated with the predictive modeling system 402 with patient medical data and physician information to further improve the prediction power of the predictive modeling system 402. For example, the notification system 404 may be used to aggregate prediction results at different levels (e.g., a patient level score to evaluate patient disease progression and treatment progress), which can be presented as a quantitative measurements of a patient's journey of mental health. Similarly, the prediction results may be aggregated at a physician level as a relative evaluation of consolidated physician treatment efficiency. Both data points are very informative to health plan providers, PBMs, and physicians.

Software Architecture

Figure 14:
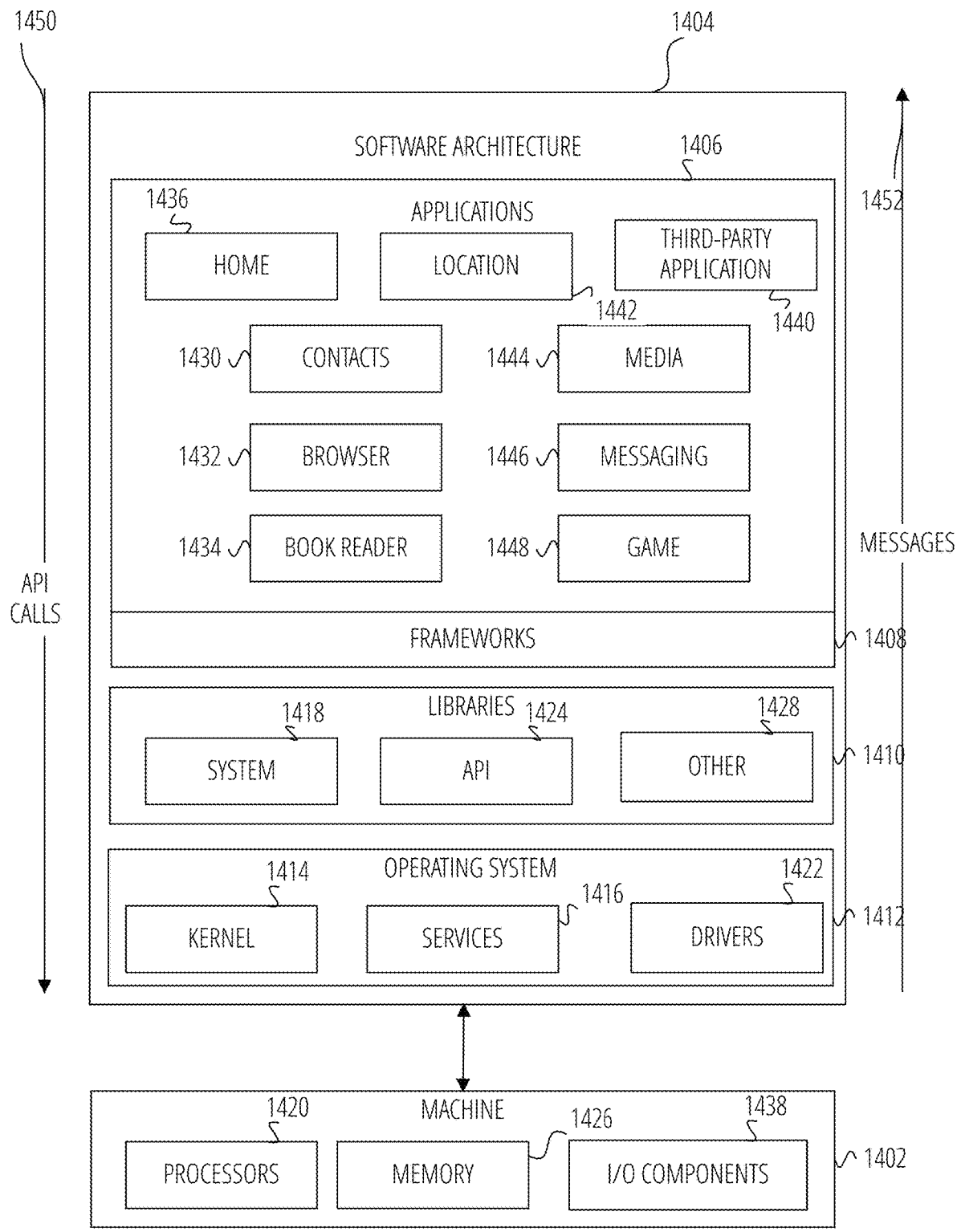
FIG. 14 is a block diagram showing a software architecture within which examples may be implemented.

FIG. 14 is a block diagram illustrating a software architecture 1404, which can be installed on any one or more of the devices described herein. The software architecture 1404 is supported by hardware such as a machine 1402 that includes processors 1420, memory 1426, and I/O components 1438. In this example, the software architecture 1404 can be conceptualized as a stack of layers, where each layer provides a particular functionality. The software architecture 1404 includes layers such as an operating system 1412, libraries 1410, frameworks 1408, and applications 1406. Operationally, the applications 1406 invoke API calls 1450 through the software stack and receive messages 1452 in response to the API calls 1450.

The operating system 1412 manages hardware resources and provides common services. The operating system 1412 includes, for example, a kernel 1414, services 1416, and drivers 1422. The kernel 1414 acts as an abstraction layer between the hardware and the other software layers. For example, the kernel 1414 provides memory management, processor management (e.g., scheduling), component management, networking, and security settings, among other functionality. The services 1416 can provide other common services for the other software layers. The drivers 1422 are responsible for controlling or interfacing with the underlying hardware. For instance, the drivers 1422 can include display drivers, camera drivers, BLUETOOTH® or BLUETOOTH® Low Energy drivers, flash memory drivers, serial communication drivers (e.g., USB drivers), WI-FI® drivers, audio drivers, power management drivers, and so forth.

The libraries 1410 provide a common low-level infrastructure used by the applications 1406. The libraries 1410 can include system libraries 1418 (e.g., C standard library) that provide functions such as memory allocation functions, string manipulation functions, mathematic functions, and the like. In addition, the libraries 1410 can include API libraries 1424 such as media libraries (e.g., libraries to support presentation and manipulation of various media formats such as Moving Picture Experts Group-4 (MPEG4), Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in two dimensions (2D) and three dimensions (3D) in a graphic content on a display), database libraries (e.g., SQLite to provide various relational database functions), web libraries (e.g., WebKit to provide web browsing functionality), and the like. The libraries 1410 can also include a wide variety of other libraries 1428 to provide many other APIs to the applications 1406.

The frameworks 1408 provide a common high-level infrastructure that is used by the applications 1406. For example, the frameworks 1408 provide various graphical user interface (GUI) functions, high-level resource management, and high-level location services. The frameworks 1408 can provide a broad spectrum of other APIs that can be used by the applications 1406, some of which may be specific to a particular operating system or platform.

In an example, the applications 1406 may include a home application 1436, a contacts application 1430, a browser application 1432, a book reader application 1434, a location application 1442, a media application 1444, a messaging application 1446, a game application 1448, and a broad assortment of other applications such as a third-party application 1440 The applications 1406 programs that execute functions defined in the programs. Various programming languages can be employed to create one or more of the applications 1406 structured in a variety of manners, such as object-oriented programming languages (e.g., Objective-C, Java, or C++) or procedural programming languages (e.g., C or assembly language). In a specific example, the third-party application 1440 (e.g., an application developed using the ANDROID™ or IOS™ software development kit (SDK) by an entity other than the vendor of the particular platform) may be mobile software running on a mobile operating system such as IOS™, ANDROID™, WINDOWS® Phone, or another mobile operating system. In this example, the third-party application 1440 can invoke the API calls 1450 provided by the operating system 1412 to facilitate functionality described herein.

Machine Architecture

Figure 15:
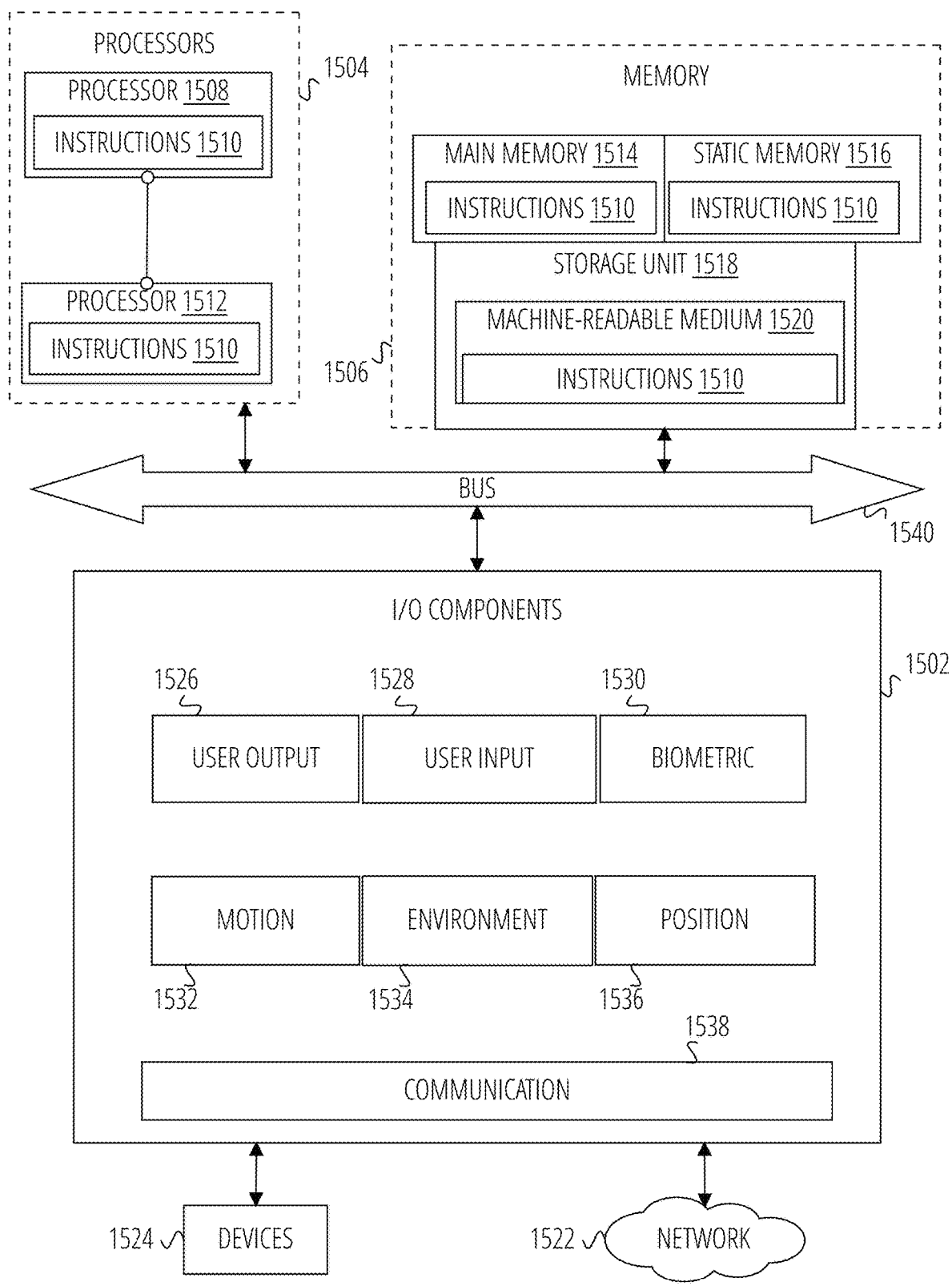
FIG. 15 is a diagrammatic representation of a machine in the form of a computer system within which a set of instructions may be executed for causing the machine to perform any one or more of the methodologies discussed herein, in accordance with some examples.

FIG. 15 is a diagrammatic representation of the machine within which instructions 1510 (e.g., software, a program, an application, an applet, an app, or other executable code) for causing the machine to perform any one or more of the methodologies discussed herein may be executed. For example, the instructions 1510 may cause the machine to execute any one or more of the methods described herein. The instructions 1510 transform the general, non-programmed machine into a particular machine programmed to carry out the described and illustrated functions in the manner described. The machine may operate as a standalone device or may be coupled (e.g., networked) to other machines. In a networked deployment, the machine may operate in the capacity of a server machine or a client machine in a server-client network environment, or as a peer machine in a peer-to-peer (or distributed) network environment. The machine may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 1510, sequentially or otherwise, that specify actions to be taken by the machine. Further, while only a single machine is illustrated, the term "machine" shall also be taken to include a collection of machines that individually or jointly execute the instructions 1510 to perform any one or more of the methodologies discussed herein. The machine, for example, may comprise the user device(s) 108 or any one of a number of server devices in mental health management system 130. In some examples, the machine may also comprise both client and server systems, with certain operations of a particular method or algorithm being performed on the server-side and with certain operations of the particular method or algorithm being performed on the client-side.

The machine may include processors 1504, memory 1506, and input/output I/O components 638, which may be configured to communicate with each other via a bus 1540. In an example, the processors 1504 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 1508 and a processor 1512 that execute the instructions 1510. The term "processor" is intended to include multi-core processors that may comprise two or more independent processors (sometimes referred to as "cores") that may execute instructions contemporaneously. Although FIG. 15 shows multiple processors 1504, the machine may include a single processor with a single-core, a single processor with multiple cores (e.g., a multi-core processor), multiple processors with a single core, multiple processors with multiples cores, or any combination thereof.

The memory 1506 includes a main memory 1514, a static memory 1516 and a storage unit 1518 both accessible to the processors 1504 via the bus 1540. The main memory 1514, a static memory 1516 and storage unit 1518 both store the instructions 1510 embodying any one or more of the methodologies or functions described herein. The instructions 1510 may also reside, completely or partially, within the main memory 1514, within the static memory 1516, within machine-readable medium 1520 within the storage unit 1518, within at least one of the processors 1504 (e.g., within the Processor's cache memory), or any suitable combination thereof, during execution thereof by the machine.

The I/O components 1502 may include a wide variety of components to receive input, provide output, produce output, transmit information, exchange information, capture measurements, and so on. The specific I/O components 1502 that are included in a particular machine will depend on the type of machine. For example, portable machines such as mobile phones may include a touch input device or other such input mechanisms, while a headless server machine will likely not include such a touch input device. It will be appreciated that the I/O components 1502 may include many other components that are not shown in FIG. 15. In various examples, the I/O components 1502 may include user output components 1526 and user input components 1528. The user output components 1526 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 1528 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 1502 may include biometric components 1530, motion components 1532, environmental components 1534, or position components 1536, among a wide array of other components. For example, the biometric components 1530 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 1532 include acceleration sensor components (e.g., accelerometer), gravitation sensor components, rotation sensor components (e.g., gyroscope).

The environmental components 1534 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., a barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

The position components 1536 include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 1502 further include communication components 1538 operable to couple the machine to a network 1522 or devices 1524 via respective coupling or connections. For example, the communication components 1538 may include a network interface component or another suitable device to interface with the network 1522. In further examples, the communication components 1538 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 1524 may be another machine or any of a wide variety of peripheral devices (e.g., a peripheral device coupled via a USB).

Moreover, the communication components 1538 may detect identifiers or include components operable to detect identifiers. For example, the communication components 1538 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 1538, such as location via Internet Protocol (IP) geolocation, location via Wi-Fi® signal triangulation, location via detecting an NFC beacon signal that may indicate a particular location, and so forth.

The various memories (e.g., main memory 1514, static memory 1516, and memory of the processors 1504) and storage unit 1518 may store one or more sets of instructions and data structures (e.g., software) embodying or used by any one or more of the methodologies or functions described herein. These instructions (e.g., the instructions 1510)), when executed by processors 1504, cause various operations to implement the disclosed examples.

The instructions 1510 may be transmitted or received over the network 1522, using a transmission medium, via a network interface device (e.g., a network interface component included in the communication components 1538) and using any one of several well-known transfer protocols (e.g., hypertext transfer protocol (HTTP)). Similarly, the instructions 1510 may be transmitted or received using a transmission medium via a coupling (e.g., a peer-to-peer coupling) to the devices 1524.

The hardware and software systems described herein, e.g., with reference to FIGS. 14 and 15, can execute a predictive modeler that uses a logistic regression model that can be self-learning to generate a predictive model to improve healthcare outcomes as described herein. Other statistical techniques can be executed by the hardware and software to produce the predictive model. In an example, the systems apply a clustering model to identify and flag patient records that have a risk. In an example, the systems can apply a forecast model deals to generate a numeric value for new health data based on learnings from the historical health data. In an example, the predictive modeler operations can be a neural network. The predictive modeler operations can use logistical regression to determine the data types to use as features in the model. The model build and verification is performed to determine what variables available in the database. The use of electronic circuitry to analyze the data are needed due to the quantity of data in the healthcare space and inability of people to see some of the relationships with in this quantity of data, data types, and data variables.

At least some examples described herein may operate to provide prediction flags for events and to provide scoring for mental health. The use of computing systems utilizing machine learning or artificial intelligence are needed due to the large quantity of data and the desire to find relationships between the data and the health of a patient. Such systems are dedicated machines. The entire database may include over a petabyte of data and, in some instances, multiple petabytes of data; accordingly, a dedicated machine is needed in some embodiments to execute the present methodologies described herein.

What is claimed is:

1. A method comprising:
   accessing, using a processor, member data and claim data associated with mental health of a patient from a database;
   determining, based on the member data, that the patient is associated with a trigger event, the trigger event being a mental health event;
   identifying, within a computing system, that a machine learning model is associated with the trigger event;
   generate, with the machine learning model, a prediction based on the member data and the claim data, wherein the prediction includes one or more of a first identification that the patient will become a chronic user of a type of medicine within a predetermined time frame, or a second identification that a modification will be made to a current medication of the patient;
   generating a notification based on the trigger event, the notification comprising the prediction;
   validating the notification based on a notification history associated with the patient; and
   transmitting the notification to a computing device to cause the computing device to display the notification.

2. The method of claim 1, wherein the member data comprises current medication data.

3. The method of claim 1, wherein the claim data comprises pharmacy claim data.

4. The method of claim 1, wherein the machine learning model is trained to analyze the member data and the claim data with the member data and the claim data being analyzed data being filtered to set an index period, a look back period and a follow up period, and wherein the machine learning model is trained on member data including at least one of patient eligibility, prescribed drugs, patient therapy, clinical exclusions, or combinations thereof.

5. The method of claim 1, wherein transmitting the notification further comprises:
storing an indication of the transmitted notification in association with the notification history associated with the patient.

6. The method of claim 1, wherein the first identification includes a first probability that the patient will become the chronic user of the type of medicine within the predetermined time frame, and the second identification includes a second probability that the modification will be made to the current medication of the patient,
wherein the method further comprises triggering the transmitting of the notification to the computing device in response to the second probability meeting a threshold.

7. The method of claim 6, wherein:
the machine learning model includes a first machine learning model and a second machine learning model,
the first machine learning model generates the first probability,
the second machine learning model generates the second probability; and
the method further comprises controlling dispensing of the medication from a pharmacy based in part on the notification.

8. The method of claim 7, wherein the computing device is associated with one or more of a health care provider of the patient or the patient.

9. The method of claim 1, further comprising initiating a campaign for a mental health solution for the patient based on the prediction.

10. The method of claim 1, wherein the validating the notification includes determining a frequency and timing of transmission of the notification to the computing device based on demographics of the patient and the medication.

11. The method of claim 1, further comprising:
validating the member data to determine that the machine learning model is capable of generating an accurate prediction from the member data,
wherein the generating the prediction includes analyzing the claim data and the member data with the machine learning model in response to the machine learning model being determined as capable of generating the accurate prediction from the member data.

12. A system comprising:
a processor; and
a memory storing instructions that, when executed by the processor, configure the system to perform operations comprising:
accessing member data and claim data associated with a patient from a database;
determining, based on the member data, that the patient is associated with a trigger event, the trigger event being a mental health event;
identifying that a machine learning model is associated with the trigger event;
generating, with the machine learning model, a prediction based on the member data and the claim data, wherein the prediction includes one or more of a first identification that the patient will become a chronic user of a type of medicine within a pre-determined time frame, or a second identification that a modification will be made to a current medication of the patient;
generating a notification based on the trigger event, the notification comprising the prediction;
validating the notification based on a notification history associated with the patient; and
transmitting the notification to a computing device to cause the computing device to display the notification.

13. The system of claim 12, wherein the member data comprises current medication data.

14. The system of claim 12, wherein the claim data comprises pharmacy claim data.

15. The system of claim 12, wherein the machine learning model is trained to analyze the member data and the claim data.

16. The system of claim 12, wherein transmitting the notification further comprises:
storing an indication of the transmitted notification in association with the notification history associated with the patient.

17. A non-transitory computer-readable storage medium, the computer-readable storage medium including instructions that when executed by a computer, cause the computer to:
access, using a processor, member data and claim data associated with a patient from a database;
determine, based on the member data, that the patient is associated with a trigger event, the trigger event being a mental health event;
identify that a machine learning model is associated with the trigger event;
generate, with the machine learning model, a prediction based on the member data and the claim data, wherein the prediction includes one or more of a first identification that the patient will become a chronic user of a type of medicine within a predetermined time frame, or a second identification that a modification will be made to a current medication of the patient;
generate a notification based on the trigger event, the notification comprising the prediction;
validate the notification based on a notification history associated with the patient; and
transmit the notification to a computing device to cause the computing device to display the notification.

18. The computer-readable storage medium of claim 17, wherein the member data comprises current medication data.

19. The computer-readable storage medium of claim 17, wherein the claim data comprises pharmacy claim data.

20. The computer-readable storage medium of claim 17, wherein the machine learning model is trained to analyze the member data and the claim data.

* * * * *